(12) United States Patent
Sauser et al.

(10) Patent No.: US 10,337,963 B2
(45) Date of Patent: Jul. 2, 2019

(54) APPARATUSES AND METHODS FOR DETERMINING PERFORMANCE PARAMETERS OF A FLEXIBLE SURFACE

(71) Applicant: HILL-ROM SERVICES, INC., Batesville, IN (US)

(72) Inventors: Frank Sauser, Cincinnati, OH (US); Charles A. Lachenbruch, Batesville, IN (US); Jon C. Tekulve, Milan, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 438 days.

(21) Appl. No.: 14/901,295

(22) PCT Filed: Jul. 9, 2014

(86) PCT No.: PCT/US2014/045893
§ 371 (c)(1),
(2) Date: Dec. 28, 2015

(87) PCT Pub. No.: WO2015/006407
PCT Pub. Date: Jan. 15, 2015

(65) Prior Publication Data
US 2016/0356676 A1    Dec. 8, 2016

Related U.S. Application Data

(60) Provisional application No. 61/845,685, filed on Jul. 12, 2013.

(51) Int. Cl.
*G01M 99/00*    (2011.01)
*G01L 1/20*     (2006.01)
(Continued)

(52) U.S. Cl.
CPC .......... *G01M 99/001* (2013.01); *A47C 31/123* (2013.01); *A61G 7/05* (2013.01);
(Continued)

(58) Field of Classification Search
CPC ....... A47C 27/083; A47C 27/10; A47C 31/12; A47C 31/123; A61G 7/05; G01L 1/18;
(Continued)

(56) References Cited

U.S. PATENT DOCUMENTS 2,154,561 A    4/1939  Breer et al.
2,378,039 A    6/1945  Schenker
(Continued)

FOREIGN PATENT DOCUMENTS

WO        WO 95/10762      4/1995

OTHER PUBLICATIONS

PCT Search Report and Written Opinion for PCT/US2014/045893, completed Dec. 8, 2014.

*Primary Examiner* — Randy W Gibson
*Assistant Examiner* — Gedeon M Kidanu
(74) *Attorney, Agent, or Firm* — Barnes & Thornburg LLP

(57) ABSTRACT

A method is provided for determining a characteristic of a flexible surface and determining a performance parameter of the flexible surface is disclosed. The method comprises providing a test device and pressing the test device into a flexible surface, measuring the pressures at the sensing points, and determining an envelopment parameter of the surface based on the pressures. The test device comprises a plurality of sensing points extending from a bottom of the test device upwardly along a side of the test device. A test indentor comprising a shell, wherein a least a portion of the shell is generally round in shape and has an exterior, with sensing points extending along the side of the shell, each
(Continued)

sensing point is capable of detecting pressure at its location and an elastomeric material is on the exterior of the shell and adjacent the sensing points.

16 Claims, 10 Drawing Sheets

(51) Int. Cl.
*G01L 1/18* (2006.01)
*G01N 3/40* (2006.01)
*A47C 31/12* (2006.01)
*A61G 7/05* (2006.01)
*G01N 3/42* (2006.01)

(52) U.S. Cl.
CPC ............... *G01L 1/18* (2013.01); *G01L 1/205* (2013.01); *G01M 99/007* (2013.01); *G01N 3/42* (2013.01); *G01N 3/40* (2013.01)

(58) Field of Classification Search
CPC ... G01L 1/205; G01M 99/001; G01M 99/007; G01N 3/40; G01N 3/42
See application file for complete search history.

(56) References Cited

U.S. PATENT DOCUMENTS

| | | | | |
|---|---|---|---|---|
| 2,644,332 A | 7/1953 | Ulrich | | |
| 3,195,347 A | 7/1965 | Janapol | | |
| 3,334,517 A | 8/1967 | Janapol | | |
| 3,413,849 A | 12/1968 | Janapol | | |
| 4,004,457 A * | 1/1977 | Eide | .......................... | G01N 3/00 73/818 |
| 4,140,008 A * | 2/1979 | Golembeck | .......... | A47C 31/123 73/161 |
| 4,267,728 A | 5/1981 | Manley et al. | | |
| 4,503,865 A * | 3/1985 | Shishido | ............... | A61B 5/0057 600/550 |
| 4,669,302 A * | 6/1987 | Wagner | ................. | A47C 31/123 73/172 |
| 4,827,763 A | 5/1989 | Bourland et al. | | |
| 4,964,302 A | 10/1990 | Grahn et al. | | |
| 5,010,774 A | 4/1991 | Kikuo et al. | | |
| 5,148,706 A | 9/1992 | Masuda et al. | | |
| 5,253,656 A * | 10/1993 | Rincoe | ................. | A61B 5/1036 600/595 |
| 5,357,804 A | 10/1994 | Wesemann et al. | | |
| 5,375,397 A | 12/1994 | Ferrand et al. | | |
| 5,524,636 A | 6/1996 | Sarvazyan et al. | | |
| 5,970,789 A * | 10/1999 | Meyer | ..................... | A47C 31/123 73/172 |
| 6,179,790 B1 * | 1/2001 | Cundari | ............... | A61B 5/0048 600/587 |
| 6,220,088 B1 * | 4/2001 | Scales | .................. | A47C 31/123 73/172 |
| 6,585,328 B1 | 7/2003 | Oexman et al. | | |
| 6,786,083 B1 * | 9/2004 | Bain | ..................... | A47C 31/123 73/78 |
| 7,891,259 B2 * | 2/2011 | Kim | ..................... | G01M 99/001 73/172 |
| 8,770,020 B2 | 7/2014 | Oexman et al. | | |
| 2004/0068203 A1 * | 4/2004 | Gellman | .................. | A61B 5/22 600/587 |
| 2006/0162464 A1 * | 7/2006 | Hayashi | ................... | A61B 5/16 73/818 |

* cited by examiner

1

APPARATUSES AND METHODS FOR DETERMINING PERFORMANCE PARAMETERS OF A FLEXIBLE SURFACE

CROSS-REFERENCE TO RELATED APPLICATIONS

The present application is a U.S. national counterpart application of international application serial no. PCT/US2014/045893 filed Jul. 9, 2014, which claims, under 35 U.S.C. § 119(e), the benefit of and priority to U.S. Provisional Application No. 61/845,685 filed on Jul. 12, 2013, the contents of which are hereby incorporated herein by reference.

BACKGROUND OF THE DISCLOSURE

This disclosure relates generally to methods and apparatus for determining performance parameters of patient support surfaces, such as mattresses, cushions, or pads for example. More particularly, but not exclusively, one illustrative embodiment relates an apparatus and method for determining an envelopment parameter of a patient support surface using a test apparatus and method. Moreover, another illustrative embodiment relates to determining an envelopment parameter of a patient support surface and modifying a structural or operational feature of the surface in response to the test results.

While various test methods and apparatuses have been created for determining characteristics of patient support surfaces, there is still room for improvement. Thus, a need persists for further contributions in this area of technology.

SUMMARY OF THE DISCLOSURE

In one embodiment, a method for determining a characteristic of a flexible surface is provided. The method comprises providing a test device at least part of which having a bottom area and side area. The test device comprises a plurality of sensing points extending from the bottom upwardly toward the side. The method comprises pressing the test device into a flexible surface, measuring the pressures at the sensing points, and determining an envelopment parameter of the surface based on the pressures.

In another embodiment, a test indentor is provided comprising a shell, at least a portion of which is generally round in shape and having an exterior. The indentor further comprises a plurality of pressure sensor points extending along the side of the shell, each sensing point capable of detecting pressure at its location. The indentor further comprises an elastomeric material on the exterior of the shell and adjacent the sensing points.

In a further embodiment, a method of manufacturing a sensored indentor is provided. The method comprises providing a shell, securing pressure sensors to the exterior of the shell, placing the shell into a mold while maintaining a gap between the shell and the mold. The method further comprises pouring a fluid material into the gap, and allowing the fluid material to cure.

In another embodiment, a method for determining a characteristic of a patient support surface is provided. The method comprises pressing a test device into a patient support surface, wherein at least part of the test device has a generally rounded shape having a bottom area and a side area. The test device comprises a plurality of sensing points extending from the bottom upwardly toward the side. The method further comprises measuring the pressures at the sensing points, transmitting signals representing the pressures from the sensing points to a data device, storing pressure data representing the pressures in the data device, and determining an envelopment parameter of the surface based on the pressure data.

Additional features, alone or in combination with any other feature(s), including those listed above and those listed in the claims and those described in detail below, can comprise patentable subject matter. Others will become apparent to those skilled in the art upon consideration of the following detailed description of illustrative embodiments exemplifying the best mode of carrying out the invention as presently perceived.

BRIEF DESCRIPTION OF THE DRAWINGS

Referring now to the illustrated examples in the drawings, wherein like numerals represent the same or similar elements throughout.

DETAILED DESCRIPTION OF THE ILLUSTRATED EMBODIMENTS

Figure 1:
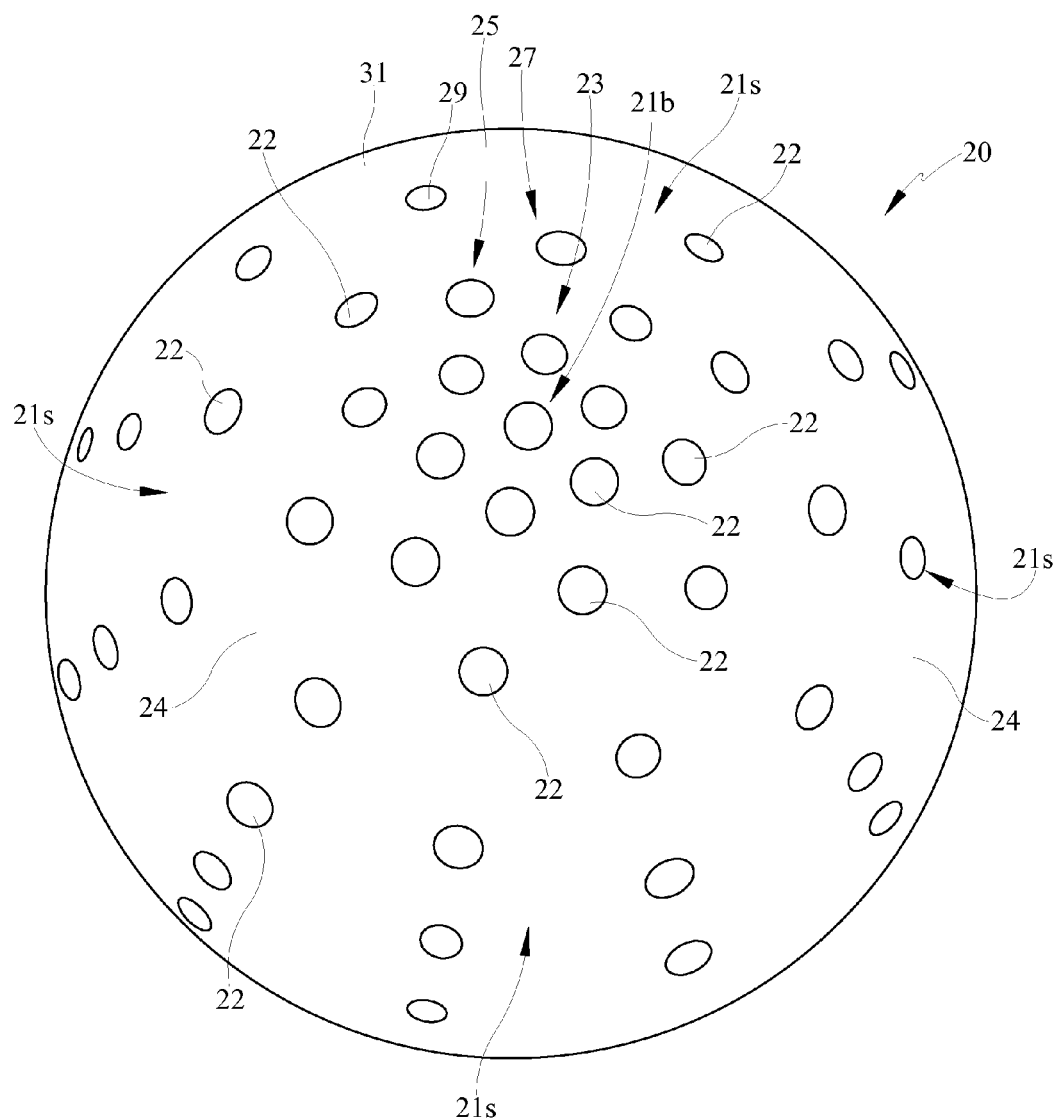
FIG. 1 is a bottom view of an illustrative embodiment of a sensored indentor, made and operating according to one or more principles of the present disclosure.

Embodiments that incorporate one or more principles of the present disclosure can take many different forms. However, for the purpose of promoting an understanding of the principles of the disclosure, reference will now be made to the embodiments illustrated in the drawings, and specific language will be used to describe the same. No limitation of the scope of the disclosure is thereby intended. Many alterations and modifications of the described embodiments, and various applications of the principles of the disclosure described herein, are contemplated.

FIG. 1 is a bottom view of an illustrative embodiment of a sensored indentor 20, made and operating according to one or more principles of the present disclosure. In this embodiment, the indentor is hemispherical in shape and includes a bottom area 21b and a side area 21s. A plurality of pressure sensors 22 are embedded in the indentor 20, beneath a layer of gel 24. The sensors 22 can be seen through the semi-transparent gel 24. Beneath the gel 24 are a rigid shell having sensors placed therein, as will be described in more detail below. The sensors 22 are spaced from the bottom/apex sensor, moving upwardly along the side 21b, in a plurality of locations (23, 25, 27, 29, 31) at known distances from the apex. As will be described in more detail below, in this embodiment the sensors 22 are placed in a plurality of concentric spaced rings moving upwardly along the hemisphere starting from the apex, the distances between the rings and the apex being known.

Figure 2:
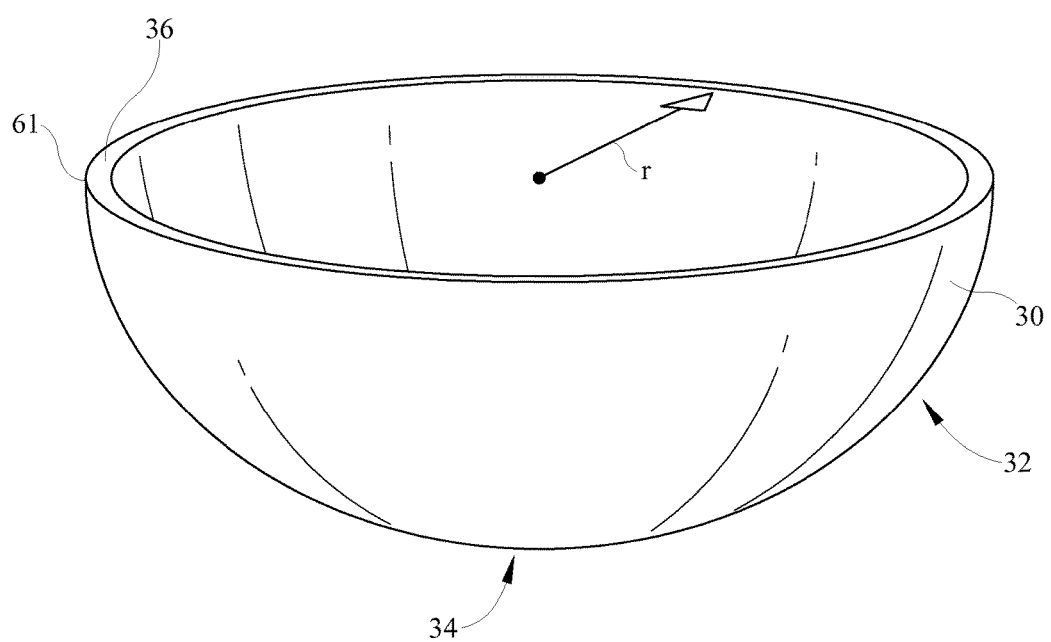
FIG. 2 is a top perspective view of the shell component of the sensored indentor of FIG. 1, prior to having holes placed therein.

FIG. 2 is a top perspective view of the shell component 30 of the sensored indentor of FIG. 1, prior to having holes placed therein. The shell 30 of this embodiment is a partial sphere and includes a bottom 34 that transitions seamlessly into sides 32. In this example, the shell includes a wall 36 that makes up the shell 30 and a hollow center surrounded by the wall 36. The shell may be made of a variety of rigid materials, such as urethane, plastic, metal, wood, composites, and the like.

Figure 3:
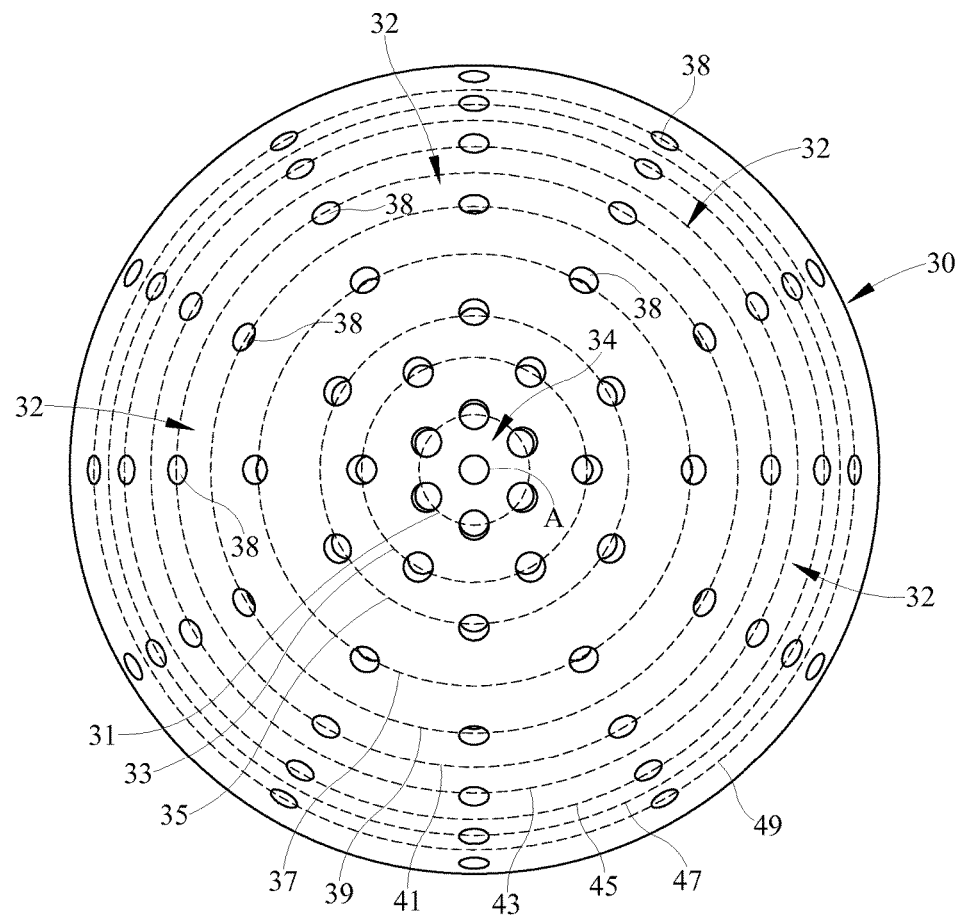
FIG. 3 is a bottom view of the shell of FIG. 2, after having holes placed therein, in a spaced and circular pattern of rings.
Figure 4:
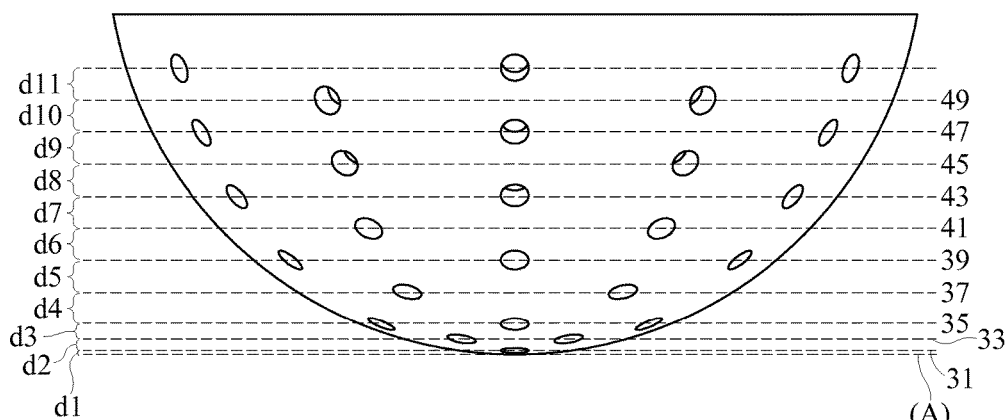
FIG. 4 is a side view of the shell of FIG. 3.

FIG. 3 is a bottom view of the shell 30 of FIG. 2, after having holes 38 placed therein, in a spaced and circular pattern of rings. An apex hole A is placed at the apex of the shell 32 in the bottom area 34. Moving upwardly from the apex hole A and along the side area 32 of the shell 30, additional holes 38 are placed along concentric rings 31, 33, 35, 37, 39, 41, 43, 45, 47, and 49 which are located at predefined or measured distances from the apex. In particular, FIG. 4 is a side view of the shell 30 of FIG. 3. As shown in FIG. 4, the distances d1-d11, between each of the rings (31, 33, 35, 37, 39, 41, 43, 45, 47, and 49) and its adjacent ring, are known, as is the overall distance of each of the rings to the Apex (A). This can be achieved, for example, by measuring off the distances d1-d11 to what is desired, and drawing or marking the rings on the shell 30. The holes 38 are then placed or formed in the shell 30, and are sized to fit corresponding pressure sensors, such as those shown in FIG. 5. The shell 30 has a radius that approximates the shape of the buttocks of a human, such as in the range of the 25-75 percentile male for example, or about the 50% male for instance. In some embodiments the radius can be selected to be between about 8 and about 12 inches, and in some embodiments can be selected to be about 10 inches.

Figure 5:
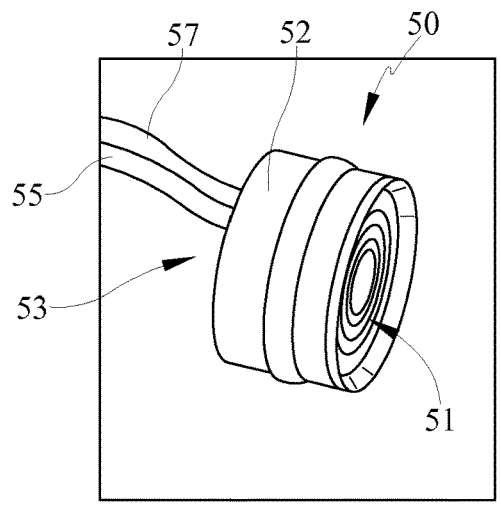
FIG. 5 is a side perspective view of one of the pressure sensors used in the sensored indentor embodiment of FIG. 1.

More particularly, FIG. 5 is a side perspective view of one of the pressure sensors 50, used in the sensored indentor embodiment of FIG. 1, and having a diameter slightly less than that of the holes 38 of the shell 30 of FIG. 4. In this embodiment, the sensor 50 is a small profile, media compatible, piezoresistive silicon pressure sensor, model 86A, made by Measurement Specialties, but many other sensors could be utilized in other embodiments. The sensor 50 includes a cylindrical body 52 and a front side 51 and back side 53. An electrical cable 55 and an air tube 57 are connected to the sensor 50.

Figure 6:
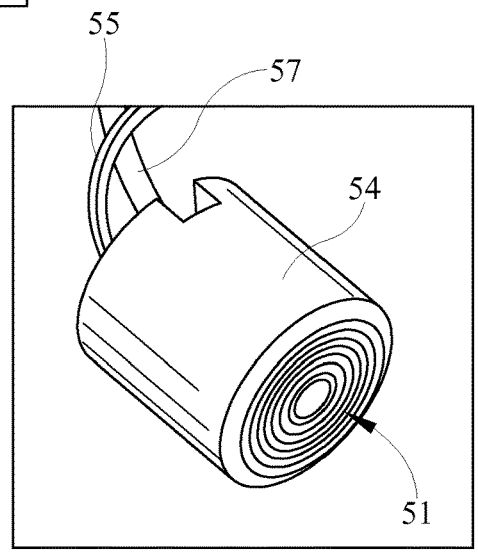
FIG. 6 is a front perspective view of the pressure sensor of FIG. 5, but with the sleeve applied.

FIG. 6 is a front perspective view of the pressure sensor 50 of FIG. 5, but with a sleeve 54 applied to provide a tight seal with the holes 38 in the shell 30 of FIG. 4. The sleeve 54 may comprise a rubber material, or other sealing material, and the sensor 50 is press fit into the sleeve. An air tube 57 is placed on the sensor vent on the back of the sensor and a silicon rubber (RTV) poured and cured 011 the back 53 of the sensor 50, lo seal the air tube to the sensor vent tube.

Figure 7:
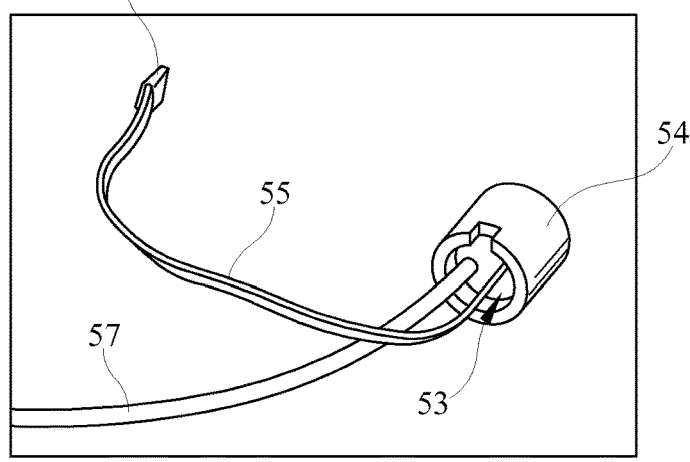
FIG. 7 is a back perspective view of the pressure sensor of FIG. 5, with the sleeve applied and showing the electrical cable and its connector, and the calibration air tube.

FIG. 7 is a back perspective view of the pressure sensor 50 of FIG. 5, with the sleeve 54 applied and showing the air tube 57, and the electrical cable 55 which terminates in an electrical connector 59.

Figure 8:
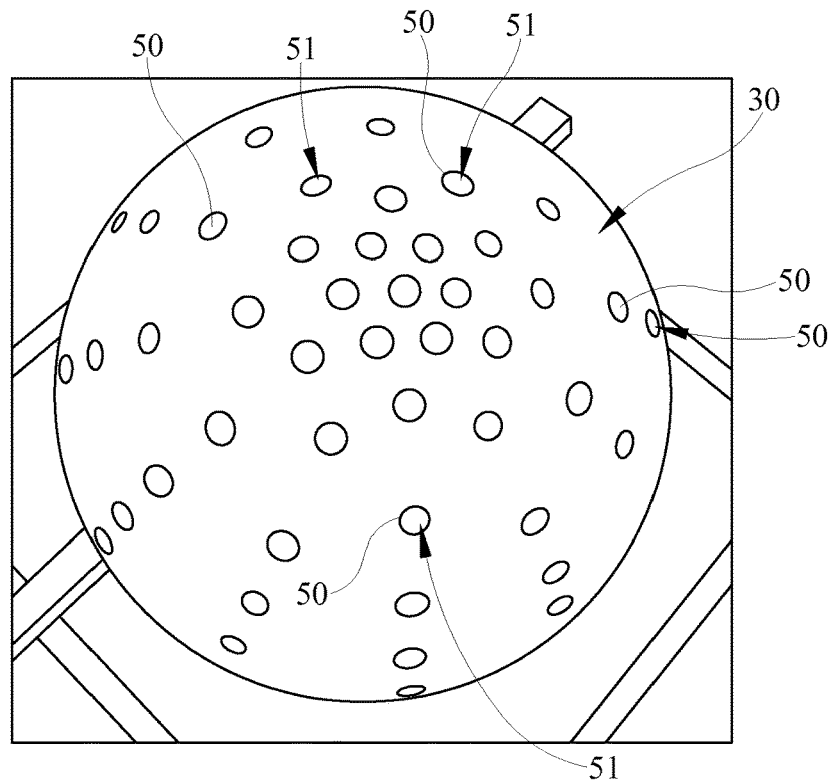
FIG. 8 is bottom perspective view of the shell of FIG. 3, with the sensors of FIG. 7 placed in the holes.

FIG. 8 is bottom perspective view of the shell 30 of FIG. 3, with the sensors 50 of FIG. 7 placed in the holes 38 of the shell. As seen in this Fig., the front side 51 of the sensors 50 are generally flush with the exterior face of the shell 30. The rubber sleeve 54 provides a tight seal between the sensors 50 and the shell 30.

Figure 9:
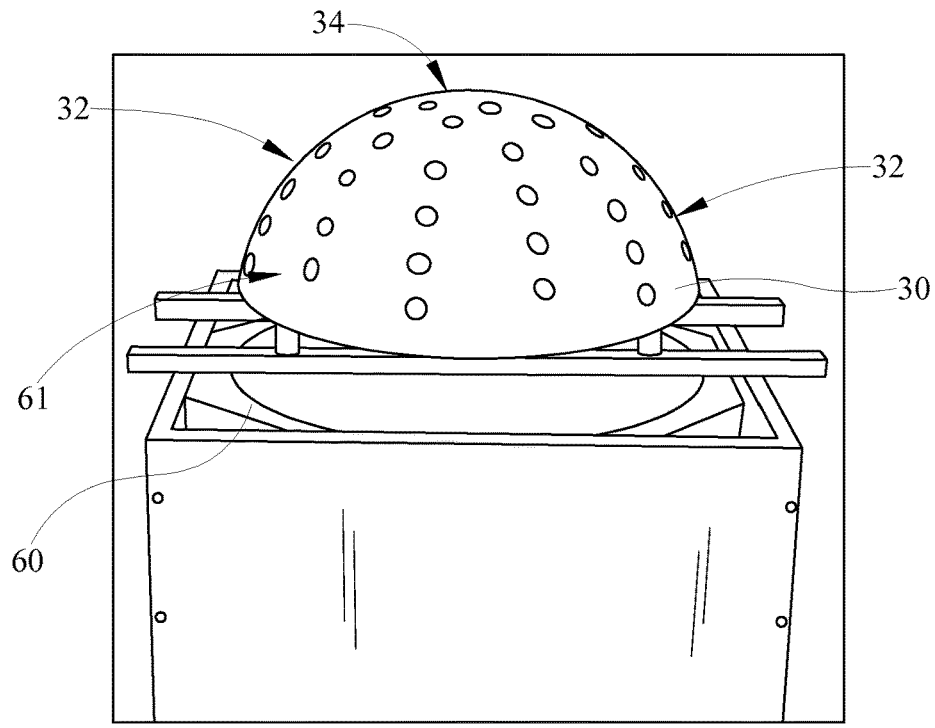
FIG. 9 is a side perspective view of the shell of FIG. 8 ready to be placed in a mold, for application of gel.

FIG. 9 is a side perspective view of the shell of FIG. 8 ready to be placed in a mold 60, and for application of gel 54. In this embodiment, the shell 30 is placed bottom 34 down into the mold 60. A gap is maintained between the mold 60 and the exterior surface 61 of the shell 30 such that a gap is present between the mold and the shell's bottom 34 and sides 32. The gap may be maintained by using a spacer (e.g. bearing or ball spacer) placed in the bottom of the mold, and a retaining structure, such as a clamp arm system for example and/or additional spacers, to measure and place/maintain the gap at the desired distance between the inside of the mold and the exterior surface 61 of the shell 30. A elastomeric material, such as a gel or gelatinous or colloidal material, primarily in fluid form (e.g., heated), is then poured in to the gap between the mold 60 and the shell 30. The gel is then allowed to cure, such that it forms the semi-solid or colloidal gel 24 of FIG. 1. The gel 24 may comprise the following formulation: 3% Dragon Skin® (Smooth-On), 15% Ecoflex® 00-10 (Smooth-On), 48% A-341 Soft Gel (Factor 2), 34% Slacker® (Smooth-on). However, other gels or sufficiently flexible materials may be used in some embodiments. In some embodiments, the gel 24 may comprise a gelatinous material that mimics or approximates the flexibility and viscosity properties of human skin and/or tissue. Once the liquid gel cures in the mold 60, the mold can be removed and the indentor 20 of FIG. 1, with sensors 22 embedded in semi-solid gel is formed. In some embodiments the gap can be in a range of suitable thickness to form a gel layer sufficient to mimic human skin and/or tissue (e.g. about ¼ to 2 inches), and in some embodiments can be about ⅜ inch.

Figure 11:
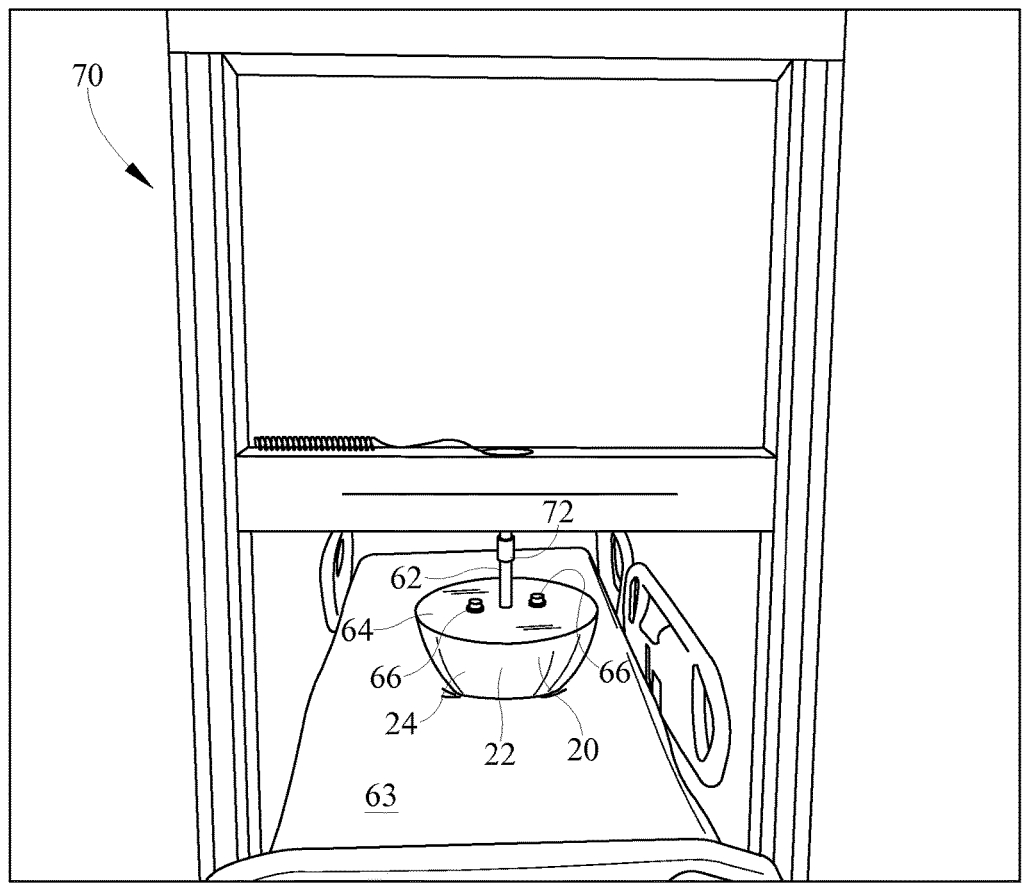
FIG. 11 is a top perspective view of the sensored indentor of FIG. 1 connected to a force displacement measuring device, and placed on a mattress for testing its contact area and envelopment.
Figure 10:
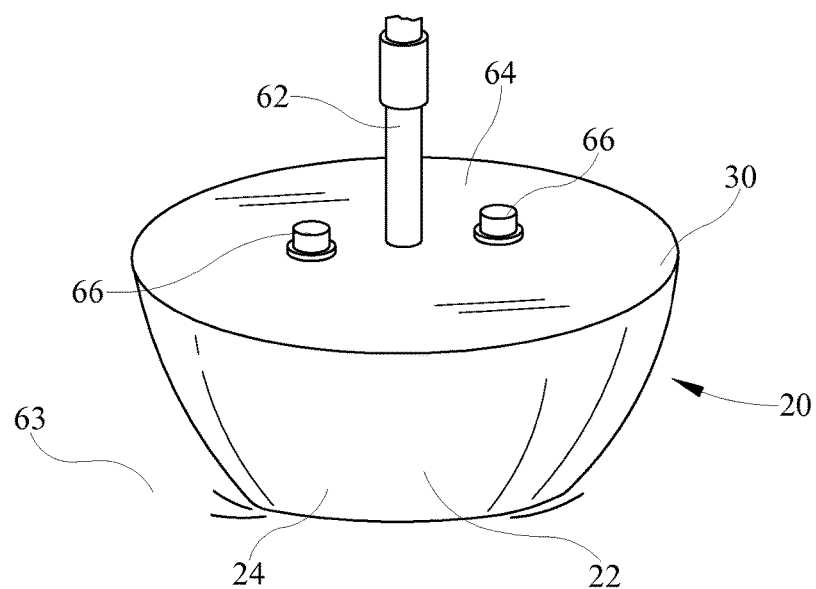
FIG. 10 is a top perspective view of the sensored indentor of FIG. 1, placed on a mattress for testing its contact area and envelopment.

FIG. 10 is a top perspective view of the sensored indentor embodiment 20 of FIG. 1, placed on a patient support surface, in this case a hospital bed mattress 63, for testing its contact area and envelopment. A cap 64 connected with a mount arm 62 are placed over the shell 30 to allow the indentor 20 to be grasped and controlled. The cap 64 includes ports 66 through which wiring and/or air tubes are allowed to exit from the indentor 20. In FIG. 10, the sensors 22 can be seen through the semi-transparent, semi-solid gel 22. FIG. 11 is a top perspective view of the sensored indentor 20 of FIG. 1 connected to a force displacement measuring device 70, and placed on the mattress 63 for testing its contact area and envelopment. In this embodiment, the indentor 20 is lined up in the center of the bed and near the hip region of the mattress, and the force displacement measuring device comprises an INSTRON® measuring system that can control displacement of its arm 72 in conjunction with the force being applied by the arm. Accordingly, the system 70 can automatically control the amount of force being applied by the indentor 20 into the flexible top surface of the mattress 63 and simultaneously electronically record the extension distance of the arm 72 at which each such force is reached. The system 70 (and/or another system) can receive the pressure readings from the sensors 22 by way of the electrical signals coming from the sensors 22, for each distance and force measured by the system 70. All of this information, and the known distances of each sensor 22 from the apex, can then be used to calculate various performance parameters of the mattress 63, including but immersion area IA of the indentor on the mattress (CA/IA). The contact area can be calculate according to the following formula:

$$CA = 2 * \pi * r * (\text{contact depth})$$

Figure 12:
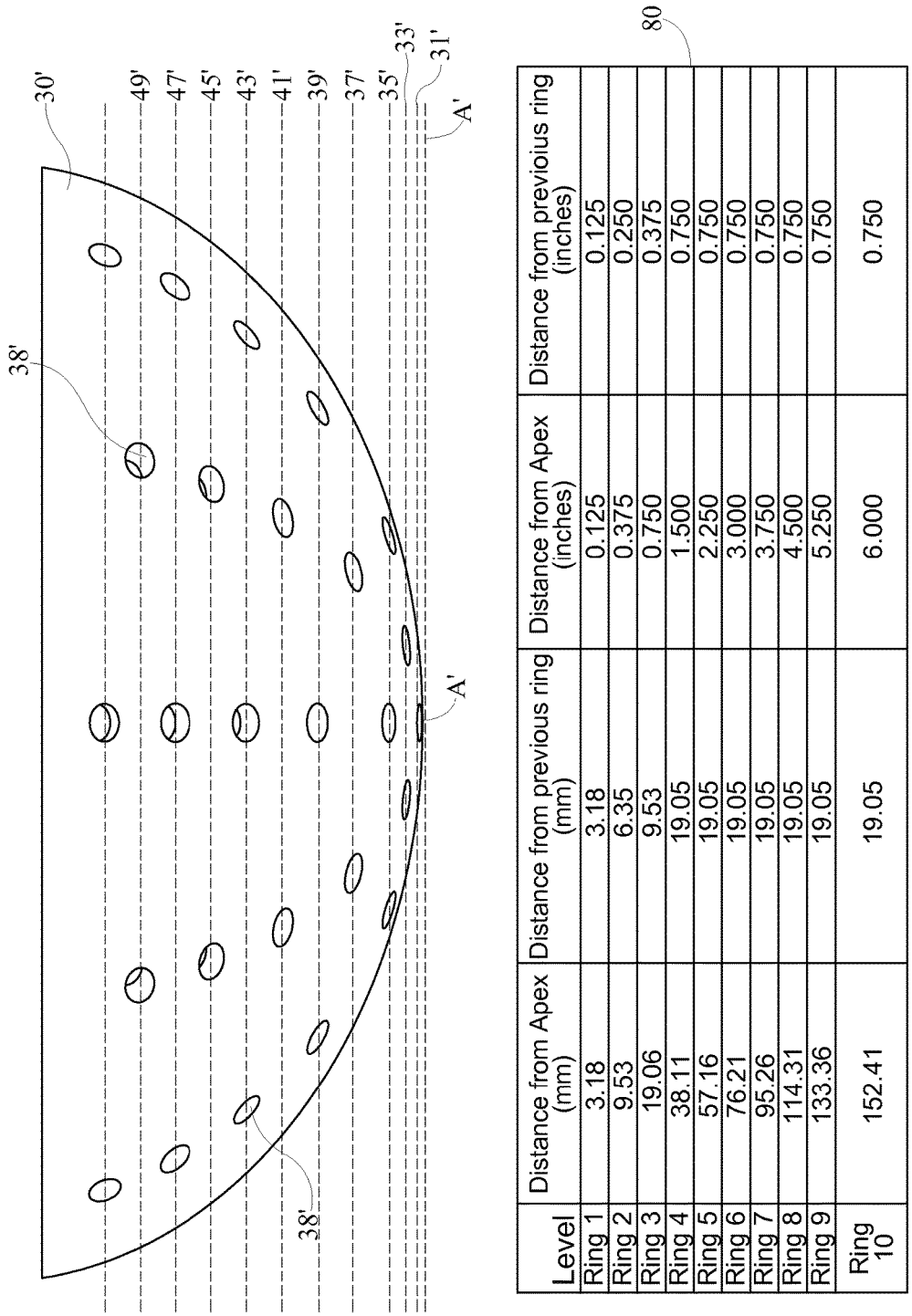
FIG. 12 is a side view of an embodiment of a shell having holes in a concentric ring pattern, made according to one or more principles of the present disclosure, and including a chart showing the distances of each ring from the apex and the previous ring.

In the embodiments of FIGS. 11 and 12, the contact depth can be determined by determining the distance of the ring of sensors to record a (greater than nominal) value from the apex of the indentor. In these embodiments, readings exceeding 1.0 mm Hg are considered to exceed nominal, and therefore to have recorded pressure. So, as an example, if it is decided to test a mattress at various forces, and the results in the table below were recorded, and if it was decided that force of most interest is 102.74 lbs, then sensor ring 6 would be chosen as the contact depth. Since it is known that sensor ring 6 is 3 inches from the apex in this example, and the radius r of the shell is known to be 10 inches, the contact area (for the 102.74 lb test) is calculated to be 188.4 square inches as shown below:

Determine Contact Depth as last ring with mean IFP>1.0 mm Hg (inches)

Contact Area=$2 * \pi *$ radius

| Mean Pressures (mm Hg) by Ring at each Instron Force Level | | | | | | | | | | | |
|---|---|---|---|---|---|---|---|---|---|---|---|
| Instron Force lbf | Base | Ring 1 | Ring 2 | Ring 3 | Ring 4 | Ring 5 | Ring 6 | Ring 7 | Ring 8 | Ring 9 | Ring 10 |
| 20.47 | 24.58 | 23.41 | 19.85 | 15.62 | 11.78 | 0.66 | −0.08 | •0.18 | •0.15 | •0.16 | •0.18 |
| 32.99 | 28.31 | 27.73 | 25.89 | 22.65 | 16.38 | 8.89 | 0.13 | •0.13 | •0.15 | •0.17 | •0.18 |
| 47.75 | 35.17 | 33.88 | 30.99 | 27.99 | 21.11 | 15.10 | 1.09 | •0.03 | •0.13 | •0.17 | •0.18 |
| 64.46 | 49.68 | 45.57 | 38.03 | 33.18 | 25.19 | 18.50 | 4.77 | 0.10 | •0.10 | •0.16 | •0.18 |
| 03.15 | 71.31 | 62.35 | 46.97 | 38.39 | 28.72 | 20.77 | 8.62 | 0.25 | •0.07 | •0.15 | •0.18 |
| 102.74 | 100.81 | 83.96 | 56.78 | 43.68 | 32.04 | 22.84 | 11.45 | 0.40 | •0.04 | •0.15 | •0.18 |
| MEAN | 51.64 | 46.15 | 36.42 | 30.25 | 22.54 | 14.46 | 4.33 | 0.07 | •0.11 | •0.16 | •0.18 |
| Dist from Apex (Ins.) | 0.00 | 0.13 | 0.38 | 0.75 | 1.50 | 2.25 | 3.00 | 3.75 | 4.50 | 5.25 | 6.00 | not limited to one or more envelopment parameters, as will be described in further detail below.

In some embodiments, the INSTRON® device can be lowered until the indentor 20 touches the mattress 63 or a strip or board placed on the mattress. At that point, the gauge length of the INSTRON® device can be reset, and any strip or board removed. The INSTRON® device can then be controlled by extension, or by force. In some embodiments, the indentor 20 can be pushed into the mattress 63 one inch at a time and held in that position for a period of time (e.g., 60 seconds) while the measurements are being made, until a certain pressure is reached (e.g., 100 mm Hg) at the apex sensor on the indentor 20. Thereafter, the indentor 20 can be extended into the mattress 63 for smaller distances (e.g., 0.25 inches) for the given time periods, while measurements continue to be taken from the sensors and the INSTRON® device, until a final pressure is reached (e.g., 150 mm Hg).

Figure 13:
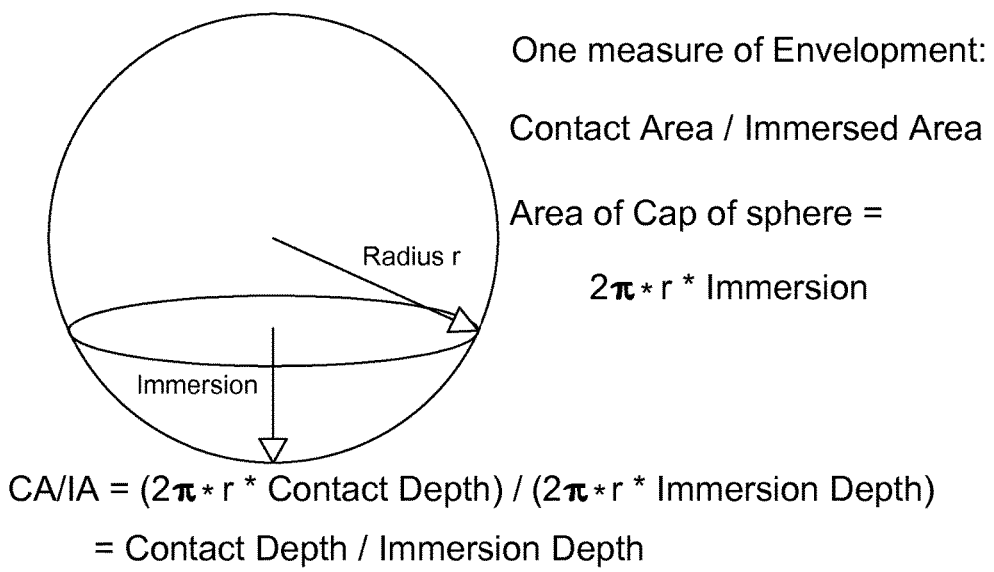
FIG. 13 is a schematic diagram of a sphere, illustrating one method of calculating envelopment of a mattress according to one or more principles of the present disclosure.

FIG. 12 is a side view of an embodiment of a shell 30' having holes in a concentric ring pattern, made according to one or more principles of the present disclosure, and including a chart showing the distances of each ring from the apex and the previous ring. These distances can be measured such that the distances are known to each pressure sensor to be held in the holes 38'. These distances can then be used to calculate performance parameters. FIG. 13 is a schematic diagram of a sphere, illustrating one method of calculating envelopment of a mattress according to one or more principles of the present disclosure. In this embodiment, an envelopment percentage EP is calculated by dividing the contact area CA of the indentor on the mattress by the Contact Area = $2 * \pi * 10.0$ inches $* 3.0$ inches $= 188.4$ inches$^2$

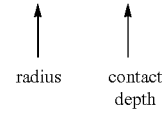

radius    contact depth

The immersion area IA for this example can be calculated as well according to the following formula:

$$IA = 2 * \pi * r * \text{immersion depth}$$

The immersion depth is known to be the depth recorded by the force displacement measuring device at the pressure of interest. In this example, if the pressure of interest was 102.74 lbs., the corresponding distance output by the measuring device is 6 inches, resulting in an immersion area of 376.8 square inches. Because envelopment percentage EP=CA/IA, the resulting EP for 102.74 lbs. for the mattress of this example is 188.4/376.8=50%

Figure 14:
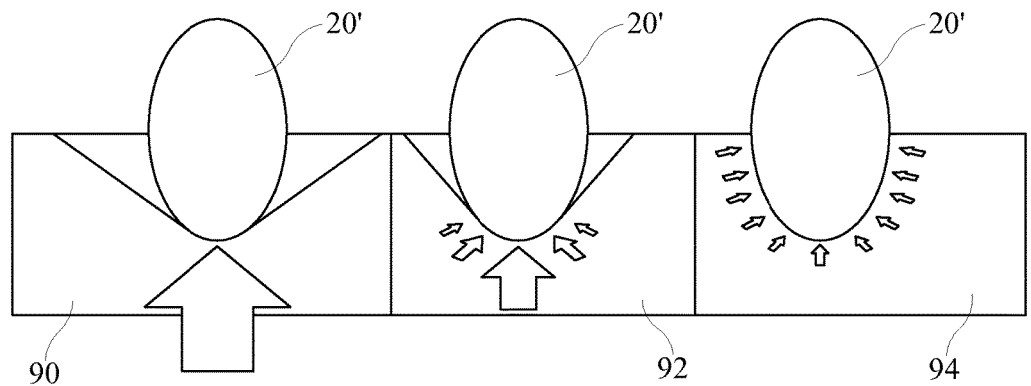
FIG. 14 is schematic illustration of three different surfaces having three different envelopment characteristics.

FIG. 14 is schematic illustration of three different flexible surfaces 90, 92, and 94 having three different envelopment characteristics when pressed by an indentor 20' at the same force. The surface 90 has small contact area CA, primarily at the bottom. The surface 92 has greater contact area CA, at the bottom and some of the immersed sides. The surface 94 has complete contact area CA at the bottom and immersed sides, corresponding to an envelopment percentage EP of 100%, such as would be obtained by a highly fluidic surface. Such characteristics can be measured by the embodiments herein, and using one or more of the principles of this disclosure.

Figure 16:
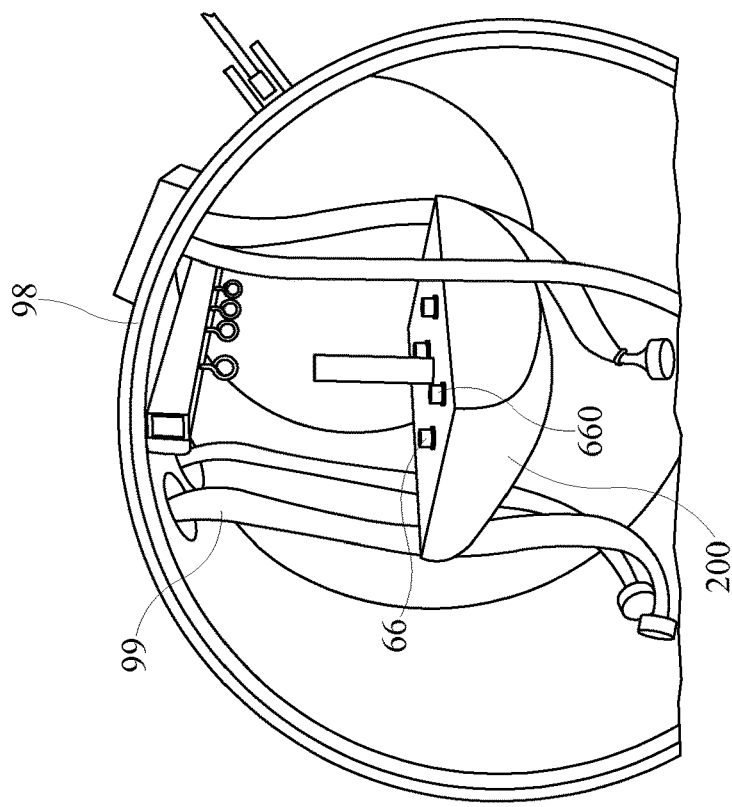
FIG. 16 is a side view of the pressure chamber of FIG. 15 but with a sensored indenter placed in the chamber.
Figure 15:
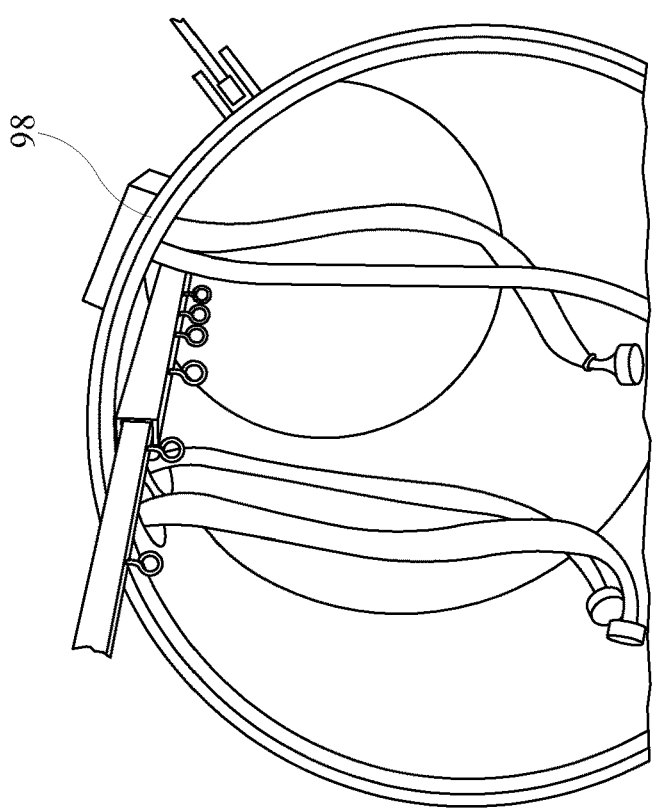
FIG. 15 is a side view of a pressure chamber that can be used for calibration of a sensored indentor according to one or more principles of the present disclosure.

Calibration of the sensors 22 of the indentor may be necessary in some circumstances. FIG. 15 is a side view of a pressure chamber 98 that can be used for calibration of a sensored indentor 200 according to one or more principles of the present disclosure. FIG. 16 is a side view of the pressure chamber 98 of FIG. 15 but with a sensored indenter 200 placed in the chamber 98. Air tubes from the sensors 22 can be run out ports 661 of the indentor 200 through exit tubes in the chamber to atmosphere. The electrical cables from the sensors 22 can be run to port 660 and connected to electrical cables 99 from the chamber. A known pressure can then be applied by the pressure chamber 98 to apply pressure to the sensors 22 of the indentor 200, and the readings from the sensors recorded by an electronic system. It can then be determined whether any sensor readings need to be adjusted (in software or on the sensor or otherwise) when using the indentor 200 for actual surface testing. The chamber 98 can be fitted with a pressure regulator as needed to control the pressure therein.

Accordingly, various flexible surfaces can be tested using one or more of the principles described herein. For example, patient support surfaces can be tested. Below is an example of results that may be obtained by using a sensored indentor such as one described herein. In the first row of this example, a selected force (such as a $50^{th}$ percentile weight load) was applied on the LAL#1 mattress resulted in an indentor immersion of 6 inches as measured by the force displacement measuring device. The contact depth for this test results in 2.25 inches in each trial. This contact depth is determined by recorded the last ring of sensors to record a pressure beyond nominal. The envelopment percentage (shown as envelopment below) for this example can then be calculated as 37.5%. Other parameters can also be calculated or otherwise determined which may be useful using one or more of the embodiments and/or principles herein. For example, the peak pressure of any given sensor may be useful for determine the peak sacral pressure performance of each mattress, under a given load (e.g., 100 lbs) using one or more of the sensored indentors described herein. For instance, the indentor 20 could be used to determine peak interface pressure by attaching the indentor to the INSTRON device, centering the indentor, bringing the indentor to touch the mattress, and resetting the gauge (as described above), and then controlling the INSTRON device to apply a load of 100 lbs for 60 seconds, and recording the peak, mean pressure (in mm Hg). As another example, the weight limit of each mattress could be measured by pushing down incrementally in force and examining the apex pressure sensor output and looking for a knee in the curve or point on the curve that represents a bottoming out or maximum pressure condition. As a further example, the indentor 20 could be used to determine contact area by attaching and centering and lowering the indentor (as described above), resetting the INSTRON gauge (as described above, and then applying a known force (e.g., 20 lbs) for a time period (e.g., 60 seconds) and continuing to apply pressure in increments (holding for the time period each) until a certain pressure is reached (e.g., equivalent to the 50th percentile weight at 45 degrees head of bed angle). The pressures from the sensors 22 can be recorded at each INSTRON pressure increment the contact area determined, such as by using the distance to the highest sensor that recorded an above nominal pressure using the one or more of the methods described herein. As also noted herein, the immersion, or depth of penetration into a surface, can be measured using one or more of the principles herein, as can envelopment or ability to conform to irregularities (or contact area for the given immersion). The force displacement measuring device, with attached indentor 20, can be controlled therefore by distance or by pressure, and can be controlled in increments and/or over time, to derive various surface performance characteristics.

| Contact Depth in inches.: (Last Ring with Mean P > 1.00 mm Hg | | | | | | | | | | | | | (Envelopment) | |
| --- | --- | --- | --- | --- | --- | --- | --- | --- | --- | --- | --- | --- | --- | --- |
| Surface | Indentor Inmerson (in.) | Trial #1 | Trial #2 | Trial #3 | Trial #4 | Trial #5 | Trial #6 | Trial #7 | Trial #8 | Trial #9 | Trial #10 | Mean | MeanImmersion % (Contact Depth/ Imm) | St Dev |
| LAL #1 (topper with spacing material) | 6.00 | 2.25 | 2.25 | 2.25 | 2.25 | 2.25 | 2.25 | 2.25 | 2.25 | 2.25 | 2.25 | 2.25 | 37.5% | 0.0% |
| LAL #2 (no topper) | 9.00 | 4.50 | 4.50 | 4.50 | 4.50 | 4.50 | 4.50 | 4.50 | 4.50 | 4.50 | 4.50 | 4.50 | 50.0% | 0.0% |
| Visco Foam | 5.25 | 3.00 | 3.00 | 3.00 | 3.00 | 3.00 | 3.00 | 3.00 | 3.00 | 3.00 | 3.00 | 3.00 | 57.1% | 0.0% |
| Gel | 6.00 | 3.00 | 3.00 | 3.00 | 3.00 | 3.00 | 3.00 | 3.00 | 3.00 | 3.00 | 3.00 | 3.00 | 57.1% | 0.0% |
| Zoned foam | 5.25 | 3.00 | 3.00 | 3.00 | 3.00 | 3.00 | 3.00 | 3.00 | 3.00 | 3.00 | 3.00 | 3.00 | 57.1% | 0.0% |
| AFT-Head | 5.00 | 5.00 | 5.00 | 5.00 | 5.00 | 5.00 | 5.00 | 5.00 | 5.00 | 5.00 | 5.00 | 5.00 | 100.0% | 0.0% |
| AFT - foot | 5.00 | 5.00 | 5.00 | 5.00 | 5.00 | 5.00 | 5.00 | 5.00 | 5.00 | 5.00 | 5.00 | 5.00 | 100.0% | 0.0% |

Figure 17:
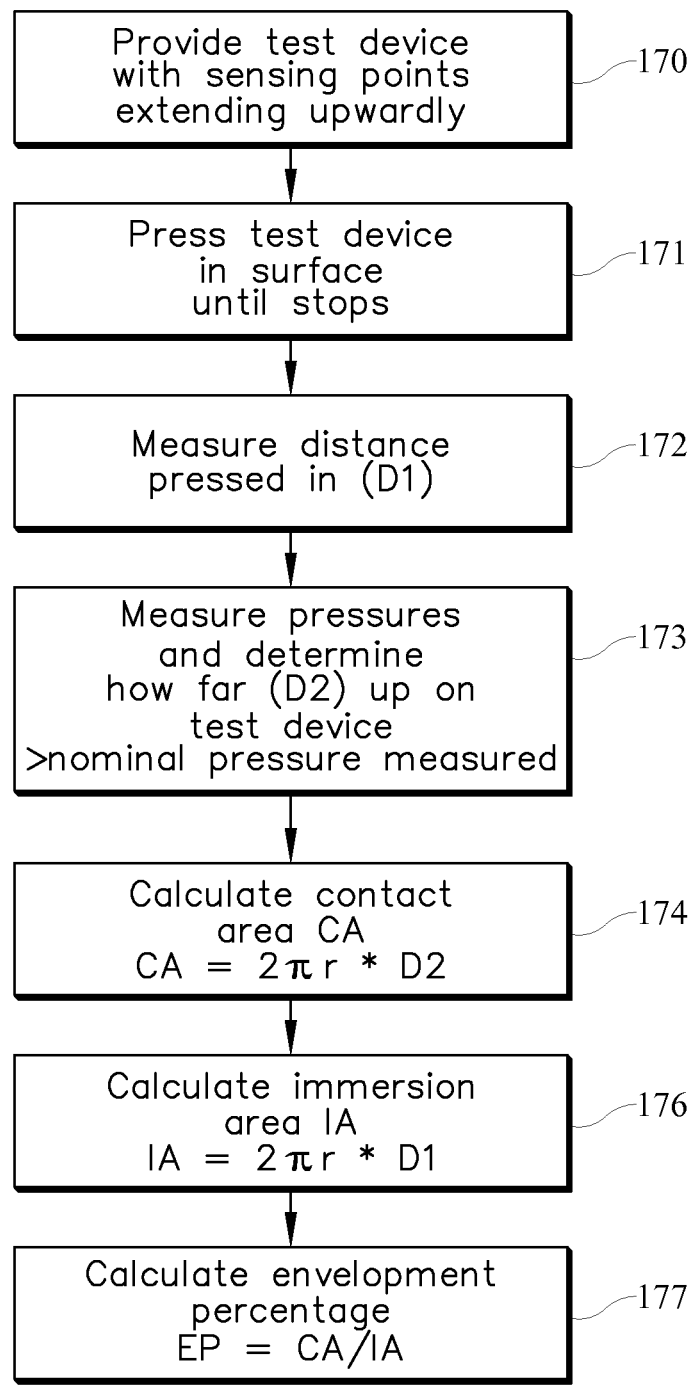
FIG. 17 is a flow diagram illustrating one illustrated method of calculating contact area, immersion area, and an envelopment parameter (in this case an envelopment percentage), according to one or more principles of the present disclosure.

FIG. 17 is a flow diagram illustrating one illustrated method of calculating contact area, immersion area, and an envelopment parameter (in this case an envelopment percentage), according to one or more principles of the present disclosure. In this example, a test device is provided, as shown at block 170. The test device includes sensing points extending upwardly. As shown at block 171, the test device is pressed into a flexible surface. The distance D1 that the device gets pressed into the surface is recorded, at block 172. As shown at block 173, the pressures from the sensing points are measured and it is determined how far up D2 on the test device that a greater than nominal pressure is measured. From D2, contact area is calculated, at block 174. From D1, immersion area IA is calculated, as shown at block 176. From CA and IA, an envelopment percentage EP is calculated as shown at block 177.

The embodiments above, and additional embodiments, can be known and understood from the attached Appendix A. One or more of the disclosures and aspects of Appendix A can be used in conjunction or as an alternative to one or more of the aspects of the embodiments described herein, as will be understood.

As can be understood, the functionality of the methods and operations described herein can be implemented using suitable software, firmware, and/or associated electronics hardware for carrying out the desired tasks. For instance, the various functionalities described can be programmed as a series of instructions, code, files, or commands using general purpose or special purpose programming languages or programs, and can be executed on one or more general purpose or special purpose computers, processors, devices, other control circuitry, or networks.

As can also be understood from reviewing the various embodiments above, many additional embodiments other than those described herein are possible and still included in the spirit and scope of the claims defining the inventions herein. For instance, sensors other than pressure sensors could be utilized, such as shear sensors for example, in some embodiments. In some embodiments, patient or patient support apparatuses can comprise beds, stretchers, chairs, lifts, or equipment to support or transport a patient, for example, or other apparatuses. The support surface, in some embodiments, can comprise a deck, cushion, frame, seat, or mattress, or portion thereof, or other surface positioned to support the patient.

Any theory, mechanism of operation, proof, or finding stated herein is meant to further enhance understanding of principles of the present disclosure and is not intended to make the present disclosure in any way dependent upon such theory, mechanism of operation, illustrative embodiment, proof, or finding. In reading the claims it is intended that when words such as "a," "an," "at least one," "at least a portion" are used there is no intention to limit the claim to only one item unless specifically stated to the contrary in the claim. When the language "at least a portion" and/or "a portion" is used the item can include a portion and/or the entire item unless specifically stated to the contrary.

It should be understood that only selected embodiments have been shown and described and that all possible alternatives, modifications, aspects, combinations, principles, variations, and equivalents that come within the spirit of the disclosure as defined herein or by any of the following claims are desired to be protected. While embodiments of the disclosure have been illustrated and described in detail in the drawings and foregoing description, these are to be considered as illustrative and not intended to be exhaustive or to limit the disclosure to the precise forms disclosed. Additional alternatives, modifications and variations can be apparent to those skilled in the art. Also, while multiple inventive aspects and principles have been presented, they need not be utilized in combination, and various combinations of inventive aspects and principles are possible in light of the various embodiments provided above.

What is claimed is:

1. A method for determining a characteristic of a flexible surface, the method comprising:
   providing a test device at least part of which having a bottom area and side area, the test device comprising a plurality of sensing points extending from the bottom upwardly toward the side, wherein the test device has a substantially hemispherical shape and the sensing points are arranged on the substantially hemispherical shape in a plurality of spaced, parallel rings that are centered on a radius of the hemispherical shape passing through an apex of the substantially hemispherical shape with at least two sensing points being arranged on each concentric ring;
   pressing the test device into a flexible surface;
   measuring pressures at the sensing points; and
   determining an envelopment parameter of the surface based on the pressures, wherein the determining operation comprises:
   determining a contact area of the test device using the sensing points, and the immersed area of the test device using a distance that the test device has been pressed into the flexible surface.

2. The method as recited in claim 1, wherein the determining operation comprises:
   determining a contact depth based upon the highest location of a sensing point where a nominal pressure is sensed.

3. The method as recited in claim 1, wherein the determining operation comprises:
   determining percent envelopment by dividing the contact area by the immersed area.

4. The method as recited in claim 1, wherein the test device comprises a flexible material adjacent the sensing points.

5. The method as recited in claim 4, wherein the test device comprises a hemispherical shell, wherein the flexible material comprises a gel adhered to an exterior of the shell, and wherein the sensing points comprise concentric rings of sensors spaced along the exterior of the shell.

6. A method for determining a characteristic of a patient support surface, the method comprising:
   pressing a test device into a patient support surface, wherein at least part of the test device has a generally rounded shape having a bottom area and a side area, the test device comprising a plurality of sensing points extending from the bottom upwardly toward the side, wherein the rounded shape of the test device comprises a substantially hemispherical shape and the sensing points are arranged on the substantially hemispherical shape in a plurality of spaced, parallel rings that are centered on a radius of the hemispherical shape passing through an apex of the substantially hemispherical shape with at least two sensing points being arranged on each concentric ring;
   measuring pressures at the sensing points;
   transmitting signals representing the pressures from the sensing points to a data device;
   storing pressure data representing the pressures in the data device; and
   determining an envelopment parameter of the surface based on the pressure data; wherein the envelopment parameter is determined by dividing a contact area (CA) by an immersion area (IA), wherein CA and IA are calculated by the following formulas:

$$CA = 2*\pi*r*(\text{contact depth})$$

$$IA = 2*\pi*r*(\text{immersion depth}),$$

wherein r is the radius of the generally rounded shape.

7. The method as recited in claim 6, wherein an immersion depth is calculated by measuring how far down the test device has been pressed into the support surface.

8. The method as recited in claim 6, further comprising:
   measuring an immersion depth that the test device has been pressed into support surface, wherein the envelopment parameter is further based on the immersion depth.

9. The method as recited in claim 6, wherein the pressing operation is carried out at a controlled force by a measuring device.

10. The method as recited in claim 9, wherein the measuring device comprises a force displacement measuring device.

11. The method as recited in claim 9, wherein the measuring device presses the test device into the patient support surface at a known force and records displacement data indicating how far the test device has been pressed into the patient support surface.

12. A method for determining a characteristic of a patient support surface, the method comprising:
pressing a test device into a patient support surface, wherein at least part of the test device has a generally rounded shape having a bottom area and a side area, the test device comprising a plurality of sensing points extending from the bottom upwardly toward the side, wherein the rounded shape of the test device comprises a substantially hemispherical shape and the sensing points are arranged on the substantially hemispherical shape in a plurality of spaced, parallel rings that are centered on a radius of the hemispherical shape passing through an apex of the substantially hemispherical shape with at least two sensing points being arranged on each concentric ring;
measuring pressures at the sensing points;
transmitting signals representing the pressures from the sensing points to a data device;
storing pressure data representing the pressures in the data device; and
determining an envelopment parameter of the surface based on the pressure data;
wherein the pressing operation is carried out at a controlled force by a measuring device; wherein the measuring device presses the test device into the patient support surface at a known force and records displacement data indicating how far the test device has been pressed into the patient support surface; wherein the envelopment parameter is determined based on a contact area determined from the pressure data and an immersion parameter determined from the displacement data.

13. The method as recited in claim 6, wherein the contact depth is determined by a height from the bottom of the test device of the sensing point that measures a pressure exceeding a nominal pressure.

14. A method for determining a characteristic of a patient support surface, the method comprising:
pressing a test device into a patient support surface, wherein at least part of the test device has a generally rounded shape having a bottom area and a side area, the test device comprising a plurality of sensing points extending from the bottom upwardly toward the side, wherein the rounded shape of the test device comprises a substantially hemispherical shape and the sensing points are arranged on the substantially hemispherical shape in a plurality of spaced, parallel rings that are centered on a radius of the hemispherical shape passing through an apex of the substantially hemispherical shape with at least two sensing points being arranged on each concentric ring;
measuring pressures at the sensing points;
transmitting signals representing the pressures from the sensing points to a data device;
storing pressure data representing the pressures in the data device;
determining an envelopment parameter of the surface based on the pressure data; and
measuring the immersion depth that the test device has been pressed into support surface, wherein the envelopment parameter is further based on the immersion depth; wherein the envelopment parameter is an envelopment percentage (EP) determined by the following equation:

$$(2*\pi*r*(\text{contact depth}))/(2*\pi*r*(\text{immersion depth})).$$

15. The method as recited in claim 14, wherein the contact depth is determined by a distance to a highest sensing point that senses a pressure that is greater than a nominal value, and the immersion depth is determined by measuring a distance that the test device has been pressed into the patient support surface.

16. The method as recited in claim 15, wherein the distance that the test device has been pressed into the patient support surface is determined by a force displacement measuring device that automatically carries out the pressing step until a predetermined pressure is reached.

* * * * *